United States Patent [19]

Boger

[11] Patent Number: 4,964,867
[45] Date of Patent: Oct. 23, 1990

[54] PATELLAR PROSTHESIS

[75] Inventor: John W. Boger, Warsaw, Ind.

[73] Assignee: Boehringer Mannheim Corp., Indianapolis, Ind.

[21] Appl. No.: 306,440

[22] Filed: Feb. 3, 1989

[51] Int. Cl.⁵ .............................................. A61F 2/38
[52] U.S. Cl. ........................................ 623/20; 623/18
[58] Field of Search ................................. 623/20, 10

[56] References Cited

U.S. PATENT DOCUMENTS 4,158,894  6/1979  Worrell ................................. 623/20
4,281,419  8/1981  Treace ................................. 623/10

Primary Examiner—Randall L. Green
Assistant Examiner—Stephanie L. Iantorno
Attorney, Agent, or Firm—Max J. Kenemore

[57] ABSTRACT

Improved resistance to linear displacement through bone is observed in a prosthetic patellar joint when the joint is attached to the patella by a protuberance which has a concave shape.

3 Claims, 1 Drawing Sheet

PATELLAR PROSTHESIS

FIELD OF THE INVENTION

This invention relates generally to the field of prosthetic devices and more specifically to improved patellar prostheses.

BACKGROUND OF THE INVENTION

Patellar joint prostheses are not new. They have been used in the past to repair damaged or diseased knee joints, often in conjunction with other prosthetic components for a total or partial knee replacement.

A patellar joint prosthesis is normally implanted on the back of the patella to replace the natural surface which articulates with the femoral component. The surgical process includes everting the patella and removing the diseased or damaged articulating surface. The patellar joint prosthesis is then attached to the bone, and the joint is reassembled.

In the past patellar joint prostheses have comprised a relatively flat bone facing surface and a contoured surface opposite the bone facing surface. When the joint is reassembled, the contoured surface articulates with the femoral component of the knee joint, whether they are natural or prosthetic.

In the past the bone facing surface of the prosthesis included a protuberance for attaching that surface to the everted patella. The protuberances have varied in shape. The most common such protuberances are a plurality of pins, normally three or four, which are pressed into the patella. Solid shapes such as crosses have also been used.

The protuberances used in the past have been effective. However, there is always a desire to find improved means for attaching the prosthetic patellar joints to the patella. An improved means for attachment would be one which shows increased resistance to shear displacement between the prosthesis and the patella.

SUMMARY OF THE INVENTION

It is an object of the present invention to provide an improved prosthetic patellar joint implant which, after implantation, has improved resistance to lateral dislocation and to separation from the patella bone.

It is also an object of this invention to provide a surgical procedure for implanting such an improved prosthetic patellar implant.

These and other objects are accomplished by a prosthetic patellar implant comprising a bone facing surface, a contoured surface opposite the bone facing surface and a protuberance from the bone wherein the protuberance has a concave shape. In one embodiment the protuberance has a generally cylindrical cross-sectional profile, and in a preferred embodiment a portion of the cylindrical cross-sectional profile has been removed in order to permit the resulting opening to be filled with bone cement at the time of implantation.

In another aspect the present invention comprises a method for implanting the prosthetic petellar implant described above by the steps of (a) forming a recess in the patella bone suitable for receiving the concave shaped protuberance and (b) placing the concave shaped protuberance in the recess. In a preferred embodiment of this method the preferred implant, described above, is used and the cavity in its cylindrical cross-sectional profile is filled with bone cement during implantation.

BRIEF DESCRIPTION OF THE DRAWINGS

The invention is described below in greater detail with reference to the accompanying drawings in which.

DETAILED DESCRIPTION

This invention is based on the discovery that a concave protuberance on the bone facing surface of a patellar joint prosthesis provides improved resistance to lateral displacement through the patella when under stress.

Figure 1:
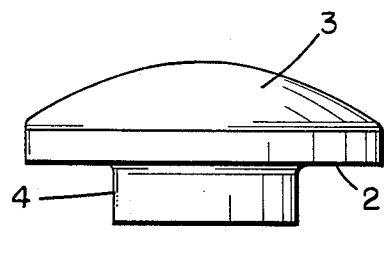
FIG. 1 shows an elevation of the improved prosthetic patellar joint implant according to the present invention.

A patellar joint implant according to the present invention is shown in FIG. 1. The implant comprises a bone facing surface 2 and a contoured surface 3 opposite the bone facing surface. Concave protuberance 4 extends from bone facing surface 2.

The prosthetic patellar joint can be made from any useful material. The selection of a particular material is not critical to this invention. The entire prosthesis can be made of, for example, metal or high density polymer. Alternatively, the prosthesis can be made two or more materials.

Figure 3:
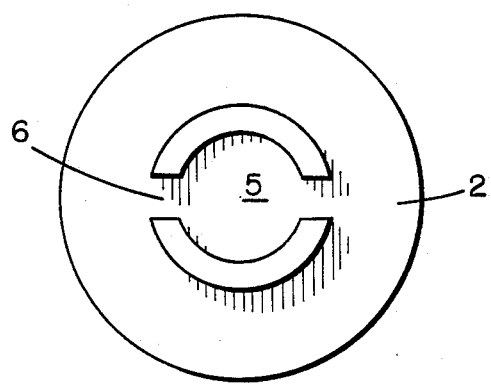
FIG. 3 shows a plan view of the bone facing surface of the implant of FIG. 2.
Figure 4:
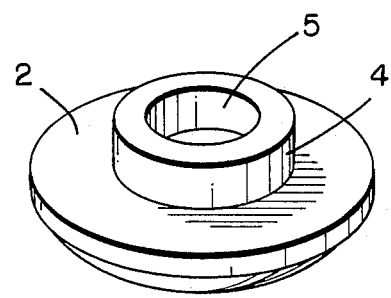
FIG. 4 shows a perspective view of a prosthesis according to the present invention as seen from the bone facing side.

Concave protuberance 4 extending from bone facing surface 2 is shown in perspective view in FIG. 4. Concave recess 5 is shown in FIGS. 3 and 5 in the center of the protuberance. In practice, recess 5 is not deeper than protuberance 4 because of the problems that would be encountered shaping the bone to receive the prosthesis if recess 5 were deeper than protuberance 4.

Protuberance 4 may be any shape which is useful to result in the formation of recess 5. For example, protuberance 4 could have a triangular, square or rectangular shape. However a circular shape which results in a cylindrical protuberance has been found to be most desirable for manufacturing reasons.

The protuberance may be any useful size depending on the size of the patella. The cylindrical protuberance shown in all of the FIGS. would have an inside diameter of about 13 mm, an outside diameter of about 18 mm and would extend about 5.5 mm from the bone facing surface.

Figure 2:
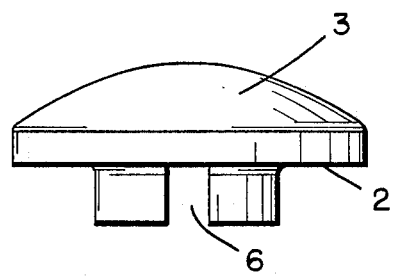
FIG. 2 shows an elevation of the preferred embodiment of the improved prosthetic patellar joint implant according to the present invention.

A preferred embodiment is shown in FIGS. 2 and 3 where openings 6 in the side of the cylindrical protuberance have been milled or cut. In use, the openings 6 are filled with bone cement which, after implantation, prevents the prosthesis from rotating.

The surgical procedure for implanting the improved prosthesis of the present invention comprises everting the patella, preparing a resected surface by removing diseased or damaged tissue therefrom, forming a recess for receiving protuberance 4, inserting protuberance 4 in the prepared recess and reassembling the joint. The recess is normally a groove having a width slightly smaller than the thickness of the walls of the protuberance. Bone cement may be applied to the groove before the patellar joint prosthesis is pressed into the groove. In a preferred surgical method, the preferred embodiment of the patellar joint prosthesis is used and bone cement is applied to the openings 6 before the prosthesis is pressed into the grooves cut into the bone.

The grooves may be cut into the patella by a surgical scalpel or by a drill, according to well known surgical techniques.

EXAMPLE

The advantages of the improvement of the present invention compared with patella prostheses of the prior art is demonstrated in the following example.

The experiment described here was designed to determine the effects of design in resisting shear displacement between patella implants and bone. Three bone-/implant interface design configurations were examined.

In each case a patella implants were obtained which were made up of a dome shaped high density polyethylene "button" and a bone facing metal portion. The bone facing metal portion was substantially flat with bone interface designs making protuberances therefrom.

The first design, designated "4-S" made use of four sharpened metal pegs approximately 2 mm in diameter and 5.5 mm long on the bone facing side of the implant. The second design, designated "4-L", made use of four sharpened pegs approximately 3.5 mm in diameter and 5.5 mm long. Designs 4-S and 4-L are typical of the prior art.

A third design in accordance with the present invention was designated "X". It had a circular protuberance with outside and inside diameters of approximately 18 mm and 13 mm and a height of approximately 5.5 mm. The circular protuberance was interrupted by an equatorial milled slot approximately 3 mm wide and the full 5.5 mm deep.

For the purposes of this experiment the metal portions of implants of the same design, as described above, were removed from the polyethylene portions and welded "face to face" so that the protuberances which differentiate the designs were extending outwardly. A rod was welded to the resulting structure to allow attachment to a testing machine. The structures were sandwiched between two slices of cancellous bone from condyles from embalmed cadaver femurs. The slices were roughly 10 mm thick and approximately 50 mm in diameter. Care was taken to insure that opposite sawn surfaces were parallel.

Prior to testing, the implant was clamped to the load cell of an MTS testing machine and a vise was clamped to a platform mounted on the piston. For designs 4-S and 4-L, the slices of bone were positioned on either side of the implant structure with the distal saw cut flat on the bottom of the vise. The vise was then tightened, driving the sharpened pegs into the bone. To avoid interference from the frictional forces between the bone and the flat surface around the protuberances, the vise was loosened slightly.

For the X design, the slices of bone were prepared to accept the concave, cylindrical protuberance prior to being put into the vise. Each slice was machined by hand using a scalpel to produce a slot equal in depth to the height of the circular protuberance and approximately one-half the thickness. After tightening in the vise, the vise was backed off slightly as for designs 4-S and 4-L.

The testing machine was operated in stroke control with the piston moving upwards at a rate of 1 mm/sec and a stroke limit of 8 mm. In this way the implant was moved proximal to distal through the bone. Force and displacement were recorded continuously on an X-Y recorder and peak force was stored in a data display unit.

Ten tests were performed using design 4-S, eight using design 4-L and 10 using design X. An average force of 153 kg was required to displace design 4-S through bone. An average force of 235 kg was required to displace design 4-L through bone. An average force of 290 kg was required to displace design X through bone. These results indicate that it would require almost twice as much force to move design X through bone as it wound to move design 4-S through bone and about 1.25 as much force as would be required for design 4-L. The comparative force required to displace the designs through bone is a good indication of their relative stability after implantation.

The present invention has been disclosed in the above teachings and drawings with sufficient clarity and conciseness to enable one skilled in the art to make and use the invention, to know the best mode for carrying out the invention and to distinguish it from other inventions and from what is old. Many variations and obvious adaptations of the invention will readily come to mind, and these are intended to be contained within the scope of the invention as claimed below.

What is claimed is:

1. A patellar prosthesis sized and shaped to be surgically implanted on the resected bone structure of a patella comprising
    a bone facing surface and a contoured surface opposite said bone facing surface;
    a protuberance extending from the bone facing surface for attaching the implant to said resected bone surface,
    the improvement characterized in that the protuberance comprises a concave shape.

2. The improvement of claim 1 wherein the protuberance has a cylindrical shape with an inner and outer diameter.

3. The improvement of claim 2 wherein at least one opening is present in the circumference of the cylindrical shape.

* * * * *